United States Patent [19]

Hergenroeder

[11] Patent Number: 4,726,363

[45] Date of Patent: Feb. 23, 1988

[54] ORTHOPEDIC CASTING APPARATUS

[76] Inventor: Patrick T. Hergenroeder, 48 W. Orange St., Chagrin Falls, Ohio 44022

[21] Appl. No.: 54,064

[22] Filed: May 19, 1987

Related U.S. Application Data

[63] Continuation of Ser. No. 791,945, Oct. 28, 1985, abandoned.

[51] Int. Cl.⁴ .................................................. A61F 5/04
[52] U.S. Cl. ........................................ 128/83; 128/82; 248/122
[58] Field of Search ................. 128/82, 83, 84 R, 133, 128/80 R, 87 R, 25 B; 24/115 H, 115 L, 136 L; 248/DIG. 4, 122

[56] References Cited

U.S. PATENT DOCUMENTS

| 449,436 | 3/1891 | Daggett . |
| 1,788,176 | 1/1931 | Sturtevant ..................... 128/25 B |
| 1,891,755 | 12/1932 | Davis . |
| 2,644,660 | 7/1953 | Dudley ......................... 248/122 |
| 3,020,909 | 2/1962 | Stevens ......................... 128/83 X |
| 3,381,684 | 5/1968 | Anderson . |
| 4,261,348 | 4/1981 | Hargadon ..................... 128/83 |
| 4,527,555 | 7/1985 | Ruf . |

Primary Examiner—Robert A. Hafer
Assistant Examiner—Kevin G. Rooney
Attorney, Agent, or Firm—Watts, Hoffmann, Fisher & Heinke

[57] ABSTRACT

An adjustable orthopedic stand with interchangeable limb-positioning attachments for maintaining an extremity in a fixed position during the application of an orthopedic cast.

19 Claims, 11 Drawing Figures

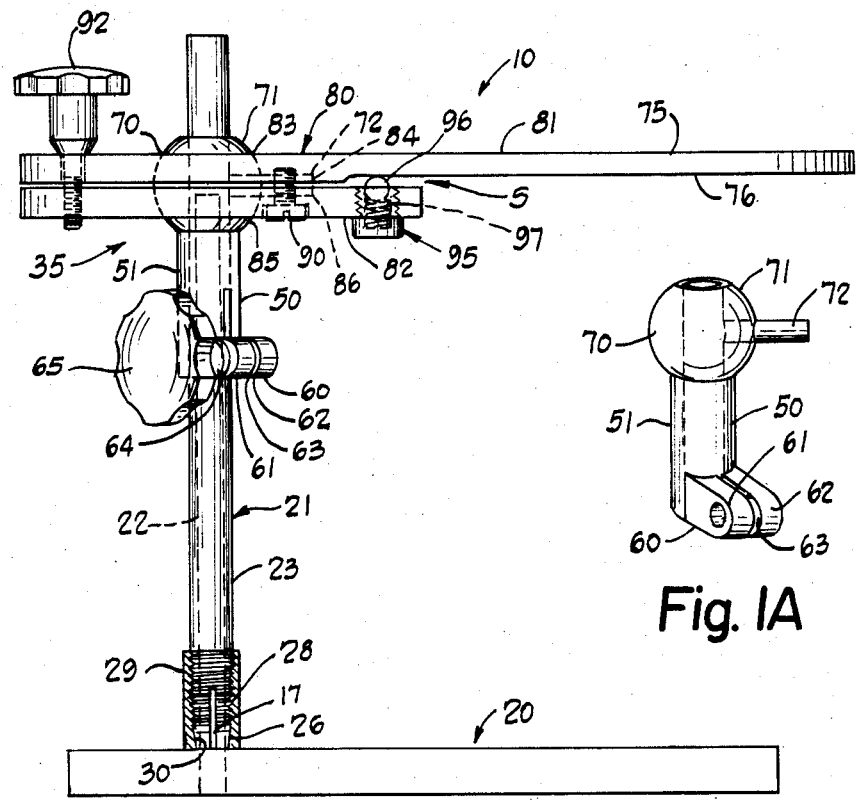
Fig. 1
Fig. 1A
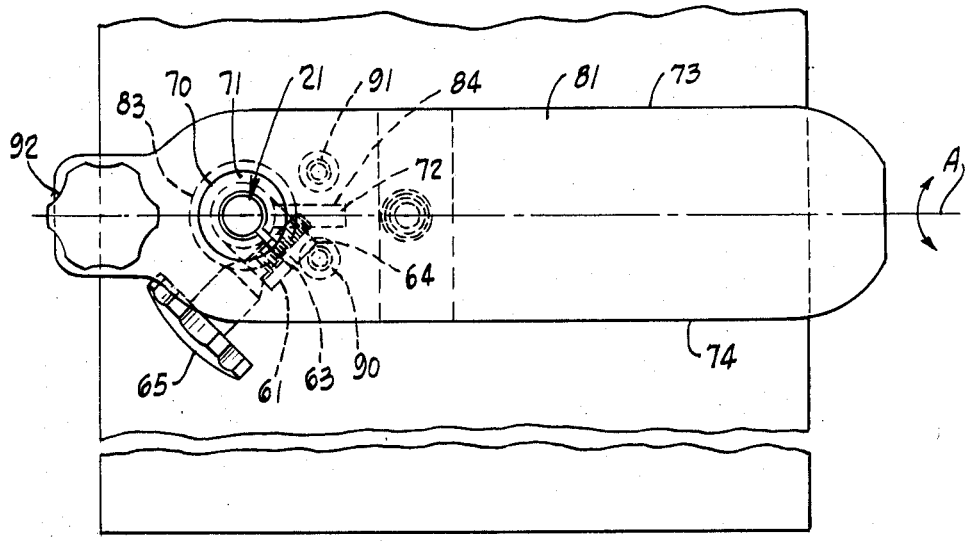
Fig. 2

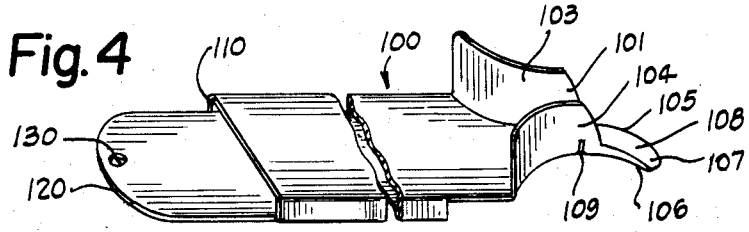
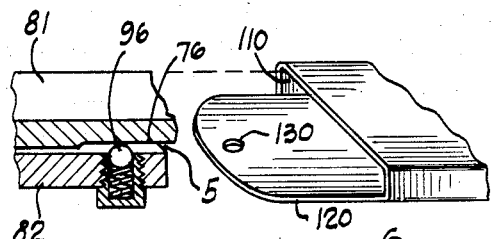
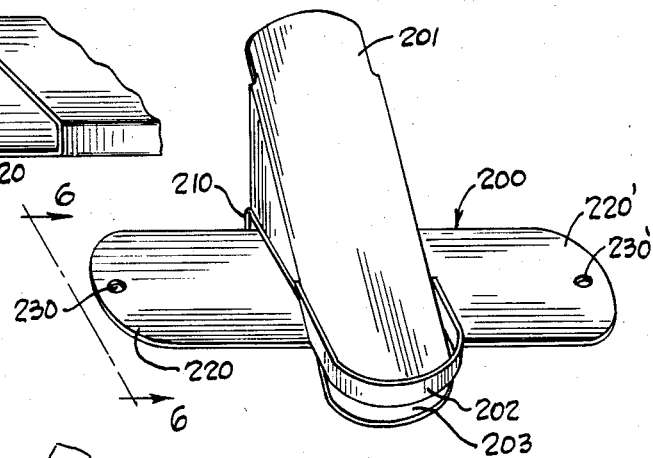
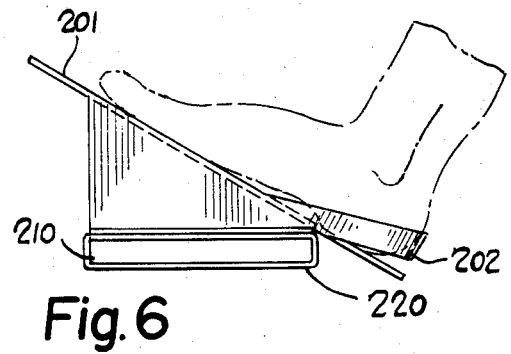
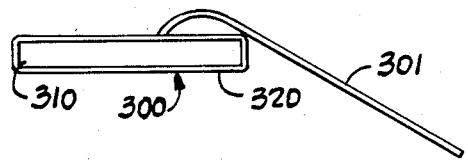
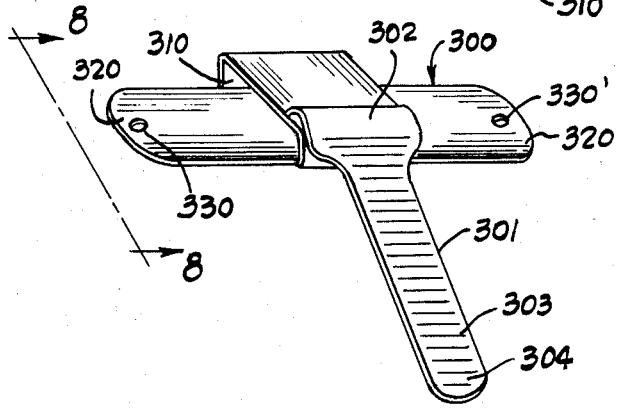

ORTHOPEDIC CASTING APPARATUS

This is a continuation of co-pending application Ser. No. 791,945 filed on Oct. 28, 1985, now abandoned.

TECHNICAL FIELD

This invention relates to an orthopedic casting apparatus and more particularly it relates to an adjustable casting apparatus with interchangeable limb-positioning attachments for maintaining an extremity in optimal joint alignment while a cast is applied.

BACKGROUND ART

The application of an orthopedic cast to an extremity requires that the extremity be positioned or immobilized in a certain attitude. The attitude is chosen to achieve optimal alignment of a joint or optimal degree of inclination of a bone to ensure that the broken parts of a bone are kept in apposition during the procedure.

A fibular or tibial fracture, for example, may require that the lower leg bones not incline from the horizontal during cast application, whereas a dislocation at the knee joint may require the lower leg bones to be positioned so as to form a knee joint angle other than ninety degrees while the cast is applied.

Injuries to the ankle may call for flexion or extension of the joint, and in some instances for inversion or eversion, while the injured joint is wrapped.

Similarly, a fracture of the lower arm bones may necessitate pronation or supenation of the forearm to put the fractured parts in apposition before a cast is applied.

DISCLOSURE OF INVENTION

The present invention provides a new orthopedic casting apparatus for maintaining an extremity in the desired position during the application of a cast.

One feature of the invention is that the casting apparatus has an adjustable limb rest to position a joint in an optimal alignment or a bone in an optimal degree of inclination.

Another feature of the invention is that the adjustable limb rest of the apparatus is adapted to engage with one of a plurality of limb-positioning attachments.

Yet another feature of the invention is that the casting apparatus can be easily and quickly adjusted to position an extremity in a certain attitude without the need for an orthopedic assistant.

A further feature of the invention is that the limb-positioning sleeves are adapted for use with either right or left extremities.

More particularly, the invention provides an orthopedic casting apparatus for use with a plurality of interchangeable limb-positioning sleeves to maintain an extremity in optimal joint alignment while a cast is applied. The orthopedic casting apparatus comprises a base, an upright attached to the base, and a limb support assembly that is moveable up and down and around the upright. The limb support assembly has a limb-supporting tongue that is pivotable about its long axis so that the angle of repose of an extremity may be adjusted. The limb-supporting tongue is adapted to support a plurality of limb-positioning sleeves.

In a preferred embodiment of the invention, the upright includes a pair of rods, one of which telescopes into the other, so that the length of the upright may be adjusted. Advantageously, this allows the option of height adjustments while maintaining a given relationship between the limb rest and the top of the upright.

In another embodiment of the invention, the limb-positioning sleeve has an arm-positioning rest extending from its proximal end. The arm-positioning rest has a narrow hand rest that is slightly concave to follow the contour of the ulnar region of the hand. The hand rest has two hand guides so that a hand reposing on the rest is maintained in the desired position between the two guides.

In yet another embodiment, the limb-positioning sleeve has a leg-positioning rest having a foot rest and a positive heel locater. The leg-positioning rest is plagioperpendicular to the leg-positioning sleeve which is engageable with the limb-supporting tongue from either side so that the foot rest and heel locator can be positioned pointing in either direction.

In a further embodiment, the limb-positioning sleeve has a foot-positioning rest plagioperpendicular to the sleeve. The limb-positioning sleeve with foot-positioning rest is engageable with the limb-supporting tongue from either side so that the foot-positioning rest can be pointed in either direction.

These and other features of the invention will be better understood from the following detailed description taken in conjunction with the accompanying drawings.

BRIEF DESCRIPTION OF THE DRAWING

FIG. 1 is a side elevational view of the orthopedic casting apparatus;

FIG. 1A is a side elevational view of a part of the apparatus of FIG. 1;

FIG. 2 is a top plan view of the apparatus of FIG. 1;

FIG. 3 is a partial perspective view, with parts in section, of the apparatus of FIG. 1 and a limb-positioning sleeve;

FIG. 4 is a partial perspective view of an arm-positioning rest of the apparatus;

FIG. 5 is a perspective view of a foot-positioning rest of the apparatus;

FIG. 6 is a side elevational view of the foot-positioning rest of FIG. 5;

FIG. 7 is a perspective view of a leg-positioning rest of the apparatus;

FIG. 8 is an end elevational view of the let-positioning rest of FIG. 7;

BEST MODE FOR CARRYING OUT THE INVENTION

Figures 9, 10:
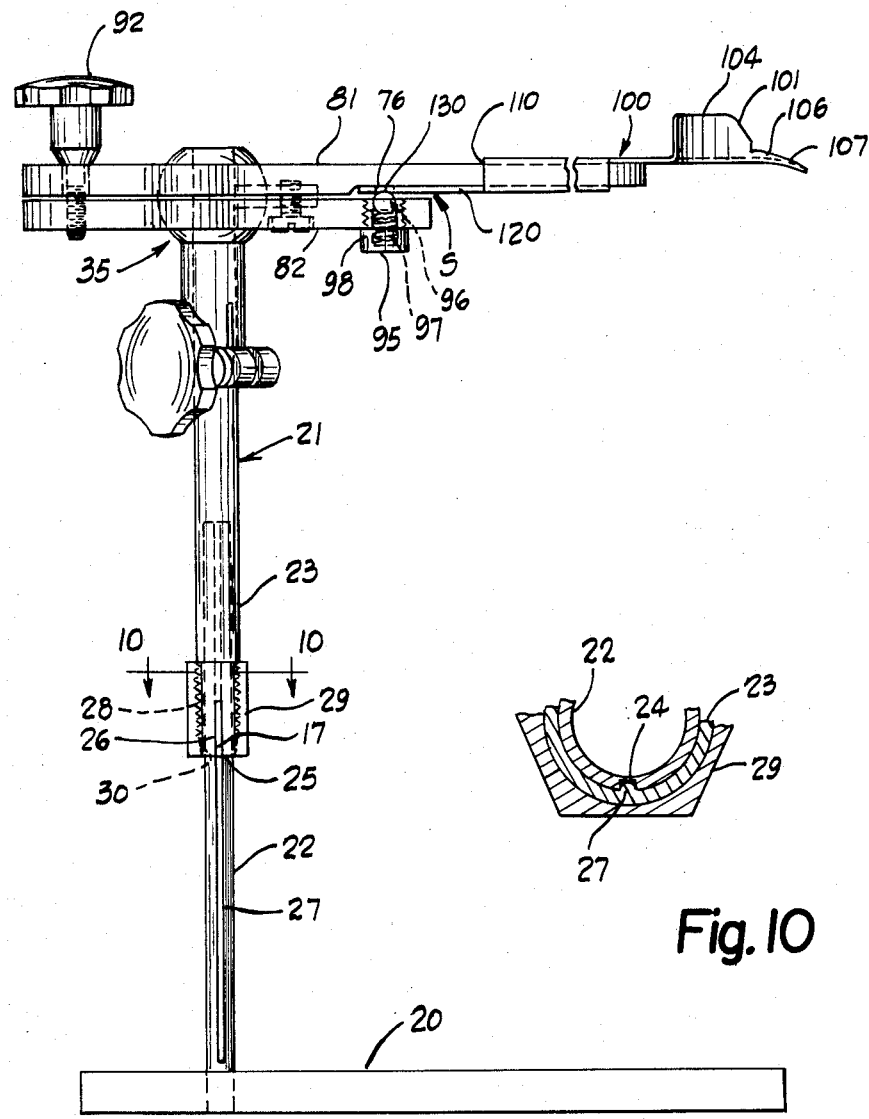
FIG. 9 is a side elevational view of the orthopedic casting apparatus with attached arm-position rest.
FIG. 10 is a partial cross sectional view of FIG. 9.

Referring now to the drawings, reference numeral 10 in FIG. 1 designates an orthopedic casting apparatus embodying the invention. The apparatus 10 is comprised of a base 20, a cylindrical upright 21, and a limb-support assembly 35.

The cylindrical upright 21 includes a first rod 22 attached to the base 20. The first rod 22 telescopes into a hollow second rod 23 through one open end 25 of the second rod 23. As shown in FIG. 10, the hollow rod 23 has an internal guide button 24 to engage an external groove 27 in the first rod 22. When the guide button 24 is engaged in the groove 27, it prevents the second rod 23 from rotating around the first rod 22 during telescoping. The end 25 of the second rod 23 has an externally tapered portion 26 with two longitudinal slots 17, only one of which is shown in FIGS. 1 and 9, and an external threaded portion 28. A threaded nut 29 screws onto the threaded portion 28 of the second rod 23. The nut 29 has an interior tapered portion, as at 30, which abuts the tapered portion 26 of the second rod 23. As the nut 29 is tightened, the interior tapered portion 30 presses against the tapered portion 26 narrowing the open end 25 so that the second rod 23 tightly grips the first rod 22 thereby fixing the cylindrical upright 21 at the desired length.

The limb-support assembly 35 which is slidable up, down and around the upright 21, comprises an adjustable carrier 50 and a limb-rest 80 pivotally connected to the adjustable carrier 50.

As shown in FIG. 1A, the adjustable carrier 50 includes a tubular member 51 defining a clamping arrangement 60 at one end for adjustably clamping the carrier 50 to the upright 21 and further defining a ball-like support structure 70 at the other end for pivotally supporting the limb-rest 80.

The clamping arrangement 60 is in the form of two lugs 61, 62 extending from the tubular member 51 on opposite sides of a slot 63 in the tubular member 51. A clamping screw 64 with a handwheel 65 goes through the lugs 61, 62. When the clamping screw 64 is tightened, the lugs 61, 62 are drawn together to narrow the slot 63 thereby clamping the carrier 50 at the desired position on the upright 21.

The ball-like support structure 70 has a radially projecting dowel 72 perpendicular to the tubular member 51. The dowel 72 serves to pivotally support and engage the limb-rest 80 on the ball-like support structure 70.

The limb-rest 80 includes a limb-supporting tongue 81 and an opposed clamping member 82. The limb-supporting tongue 81 and the opposed clamping member 82 are fastened together on opposite sides of the ball-like support structure 70 and on opposite sides of the dowel 72 by a pair of couplers 90, 91 in the form of machine screws on one side of the upright 21 and a handwheel screw 92 on the other side of the upright 21.

The limb-supporting tongue 81 is paddle shaped with parallel sides 73, 74 and faces 75, 76, and has a first circular aperture 83 which receives the upper part of the ball-like structure 70, and has a first dowel-receiving groove or channel 84 which pivotally engages with the upper part of the dowel 72. The clamping member 82 has a second circular aperture 85 which receives the lower part of the ball-like structure 70 and a second dowel-receiving groove or channel 86 which pivotally engages with the lower part of the dowel 72.

The dowel-receiving channels 84, 86 are shaped so that when the limb-supporting tongue 81 and the opposed clamping member 82 are fastened together on opposite sides of the dowel 72 by means of the couplers 90, 91, the dowel is received with a clearance fit in the channels 84, 86 and the limb-rest 80 is freely pivotable about the dowel 72 approximately 45 degrees in either direction from the horizontal positioning shown in FIG. 2. When the handwheel screw 92 is tightened, the limb-supporting tongue 81 and the opposed clamping member 82 are urged together so that the tongue 81 and clamping member 82 are clamped against the dowel and the limb-rest 80 is locked in the desired angular position about the axis of the dowel on the ball-like structure 70.

The limb-supporting tongue 81 serves to support a patient's arm or foot during a cast application procedure. In use, the upright 21 is adjusted to the desired length by telescoping the first rod 22 into the second rod 23 until the appropriate length is achieved. The nut 29 is then tightened so that the second rod 23 is fixed on the first rod 22. Once the upright is adjusted to the proper length, the limb-support assembly 35 is adjusted to a desired height on upright 21, is rotated to the desired position about the axis of the upright 21, and is locked in place with the handwheel 65 and clamping screw 64. The limb-support assembly base 20 preferably rests on the floor, but may rest on a table top as well. Once the desired height of the assembly 35 is fixed, the angle at which a limb rests on the limb-supporting tongue 81 is fixed by pivoting the support assembly 35 to the desired tilt and locking it in place by means of the handwheel screw 92.

If the casting procedure involves a patient's arm or hand, the operator may find it advantageous to position the assembly 35 at the top, as oriented in FIG. 9, of the upright 21 so that the second rod 23 does not extend above the assembly 35 and does not interfere with the operator's motions while a cast is applied. The extension of the telescoped rods allows the assembly 35 to be at a convenient height with the base on the floor, so that a patient can be conveniently treated while sitting in a chair or on a stool or table without the need of a table for supporting the apparatus.

When a patient's foot is in place on the limb-supporting tongue 81, the ankle joint may be inverted or everted by pivoting the limb-support assembly 35 about the axis A shown in FIG. 2 to the desired angle from the horizontal and securing the limb-support assembly 35 at that angle by rotating the handwheel screw 92. Typically, the rods 22, 23 will be fully telescoped when a patient's foot is being supported.

If it is necessary to facilitate support or to position a joint at an angle other than that provided by supporting an extremity on the limb-supporting tongue 81, a plurality of specialized limb-positioning attachments 100, 200, 300, as shown in FIGS. 4–8 are provided which are in the form of sleeves that slide over the limb-supporting tongue 81 and are partially received between the tongue and clamping member 82.

Each attachment has a tubular locating and supporting portion or sleeve 110, 210, 310 and a retaining portion 120, 220, 320. In the preferred embodiments of the leg-positioning attachment and the foot-positioning attachment shown in FIGS. 5 and 7, each attachment has a second retaining portion 220', 320'∝ extending in an opposite direction from the first from the sleeve portion. Each tubular locating and supporting portion 110, 210, 310 is shaped to closely receive the paddle-shaped limb-supporting tongue 81.

As shown in FIG. 3, the retaining portions 120, 220, 320, 220', 320' extend along the lower face 76 of the limb-supporting tongue 81, when the sleeve is received on the tongue, and extends (or where there are two, one will extend) into a spaces between the tongue 81 and the clamping member 82. A detent 95, which includes a ball 96 and a spring 97 within a recess 98, is in the clamping member 82, the ball being urged by the spring toward the surface 76 of the tongue. Each limb-positioning sleeve has an aperture 130, 230, 330, 230', 330' in the retaining portion 120, 220, 320, 220', 320' that cooperates with the spring biased ball 96, thus allowing the sleeve to be slipped into place and retained by the sleeve-engaging member 82, yet be easily removed. In use, the limb-supporting tongue 81 is received by the locating and supporting portion of the attachment and the retaining portion is received in the spaces between the clamping member 82 and the surface 76, thereby depressing the ball 96 on the spring 97 until the aperture on the retaining portion reaches the ball 96. The ball 96 engages with the retaining portion to secure the sleeve on the sleeve engaging member 82. This arrangement allows for easy removal or replacement of the sleeve.

Each of the sleeves shown in FIGS. 4–8 is constructed to facilitate positioning of a limb in a particular way. Each sleeve may be positioned at the desired height and pointed in the desired direction by sliding the limb-support assembly 35 on the upright 21 and locking it in place by rotating the handwheel 65. Furthermore, each sleeve can be pivoted to achieve an optimum angle by pivoting the limb-supporting rest 80 about the axis A shown in FIG. 2.

FIG. 4 illustrates an arm positioning attachment 100 with a hand-positioning member 101. The hand-positioning member 101 includes a pair of upper hand guides 103, 104 which maintain the hand in the desired position and a pair of lower hand guides 105, 106 which form an extension 107 shaped to support the ulnar region of the hand. The extension 107 is thin and narrow compared to the sleeve portion 110. The upper surface 108 of the extension 107 is concave and adapted to follow the contour of the ulnar region of the hand. A slit or slits as at 104 may be provided to allow casting plaster to be easily washed from the hand-positioning member 101. In use, the patient's hand is placed on the extension 107 between the hand guides 103, 104, 105, 106. For a lower arm bone fracture, for example, the forearm may be pronated or supenated to put the fractured bones in apposition by pivoting the limb-support assembly 35 about the axis shown in FIG. 2 to the desired tilt and locking it in place by means of the handwheel screw 92. The cast is wrapped around both the extension 107 and the hand. After application, the hand and cast can be pulled longitudinally off the extension 107.

FIG. 5 illustrates a leg-positioning attachment 200 having a foot support 201 with a positive heel locator 202. The heel locator 202 preferably has an opening 203 to allow any casting plaster that falls into the locator 202 to escape or be easily washed out. The foot support 201 serves to support a foot at approximately 45 degrees from the locating and supporting portion 210 of the sleeve 200. The leg-positioning attachment 200 is useful in immobilizing a leg in the desired position for upper and lower leg casting. The leg attachment 200 can be rotated about the axis shown in FIG. 2 to position the leg or knee in optimal alignment.

FIG. 7 illustrates a foot-positioning attachment 300 with a foot-rest 301 at approximately 45 degrees from the locating and supporting portion 310 of the sleeve 300. The foot-positioning attachment 300 is useful in applying casts which involve the ankle joint. The foot-rest 301 preferably has a wide portion 302 to support the plantar surface of a foot and a reduced width portion 303 narrow enough to allow application of a cast to a small foot, yet comfortably support a larger foot. The portion 303 can be provided with a plurality of horizontal grooves, as at 304, to inhibit slipping of the foot and yet facilitate cleaning. In use, a patient's foot is placed on the foot-rest 301. The ankle joint may be flexed or extended by pivoting the limb-support assembly 30 about the axis A shown in FIG. 2. Once the desired degree of flexion or extension is achieved, the limb-support assembly 35 is secured by rotating the handwheel screw 92. A cast is wrapped around both the foot-rest 301 and the foot and ankle. After application the foot and cast can be pulled downward off the foot-rest 301. The resultant ankle cast has no heel defect, since the cast is applied to the foot, ankle, leg and heel in a continuous wrapping.

As can be understood from the foregoing, the limb-supporting tongue 81 of the orthopedic casting assembly 10 serves both as a direct support for extremities and as a mounting or supporting element for a variety of specialized supports. The cooperation between the specialized supports that attach, and the pivoting limb-supporting tongue 81, and the limb-support assembly 35, slidable up, down and around the upright 21, allows for localizing extremities and for affording a way to make alignments in their positions rapidly and easily, thus making the cast application procedure less traumatic for the patient.

Variations and modifications of the invention will be apparent to those skilled in the art from the above detailed description. Therefore, it is to be understood that, within the scope of the appended claims, the invention can be practiced otherwise than as specifically shown and described.

I claim:

1. An orthopedic casting apparatus for use with a plurality of interchangeable limb-postioning attachments, whereby an extremity is maintained in optimal joint alignment during the application of a cast, comprising:
   a base;
   an upright attached to said base;
   a limb-support assembly having an elongated limb-rest defining a support plane; and
   a plurality of different limb-positioning attachments; said limb-rest having a long axis located substantially in the support plane, said limb-rest being pivotable about the long axis and adapted to support either an extremity or one of said limb-positioning attachments; said limb-support assembly being rotatably and vertically movable on said upright, and said assembly including means for releasably retaining one of said plurality of different limb-positioning attachments on said limb rest.

2. An orthopedic casting apparatus for maintaining an extremity in optimal joint alignment during the application of a cast comprising:
   a base;
   an upright attached to said base; and
   an elongated limb-rest movably secured to said upright and extending transversely thereof, said limb-rest defining a support plane and being pivotable about its long axis located substantially in the support plane to position an extremity resting thereon at a desired angle.

3. An orthopedic casting apparatus for use with a plurality of interchangeable limb-positioning attachments, whereby an extremity is maintained in optimal joint alignment during the application of a cast, comprising:
   a base;
   an upright mounted on said base; and
   a limb-support assembly vertically adjustable on said upright, said assembly including an elongated limb-rest movably secured to said upright and extending tranversely thereof, said elongated limb-rest defining a support plane and having a long axis located substantially in the support plane, said limb-support assembly being pivotable about the long axis of the limb rest, and said limb-support assembly having means to releasably engage one of a plurality of different limb-positioning attachments.

4. An orthopedic casting apparatus for maintaining an extremity in optimal joint alignment during the application of a cast comprising:
   a base;
   an upright attached to said base;
   a limb-support assembly movably mounted on said upright, said assembly including an elongated limb-rest defining a support plane, having a long axis located substantially in the support plane and being pivotable about the long axis relative to the upright, said assembly having limb-positioning attachment-engaging means; and
   a limb-positioning attachment releasably engageable with said limb-support assembly, said limb-positioning attachment including a limb-engaging surface to support a limb extremity resting on the surface in a desired position.

5. The orthopedic casting apparatus as claimed in claim 4 wherein the limb-support assembly has a spring-biased ball defining a spring detent and the limb-positioning attachment includes means extending from the attachment engageable and retainable by the spring detent.

6. The orthopedic casting apparatus as claimed in claim 5 wherein the means extending from the attachment to be engaged and retained bY the spring detent extend from opposite ends of the attachment.

7. An orthopedic casting apparatus as claimed in claim 4 wherein the limb-positioning attachment comprises an arm-positioning attachment including:
   a first portion adapted to connect to the limb-support assembly in releasable engagement;
   a hand-supporting portion integral with and extending from said first portion; and
   a pair of substantially parallel hand guides extending from and on either side of said hand-supporting portion to maintain a hand resting on said hand-supporting portion in the desired position.

8. The orthopedic casting apparatus as claimed in claim 7 wherein the hand-supporting portion is adapted to conform to the contour of the ulnar region of the hand.

9. An orthopedic casting apparatus as claimed in claim 4 wherein the limb-positioning attachment comprises a leg-positioning attachment including:
   at least one portion adapted to connect to the limb-support assembly in releaseable engagement; and
   a foot-supporting member plagioperpendicularly mounted on said attachment member, said foot-supporting member having a positive heel locator to maintain a foot resting on said foot-supporting member in the desired plane.

10. An orthopedic casting apparatus as claimed in claim 4 wherein the limb-positioning attachment comprises a foot-positioning attachment including:
    at least one portion adapted to connect to the limb-support assembly in releasable engagement; and
    a foot-supporting member plagioperpendicularly mounted on said attachment member.

11. The orthopedic casting apparatus as claimed in claim 10 wherein the foot-supporting member has surface means to resist slipping to frictionally maintain a foot resting on said foot-supporting member in a desired plane.

12. The orthopedic casting apparatus as claimed in claims 4, 5, 6, 10 or 11 wherein one of the limb-support assembly and limb-positioning attachment is a sleeve that slides over the other.

13. The orthopedic casting apparatus as claimed in claims 4, 5, 6, 10 or 11 wherein the upright attached to the base is a telescoping rod having means to adjustably extend or contract the length of said upright.

14. An orthopedic casting apparatus for use with a plurality of interchangeable limb-positioning attachments, whereby an extremity is maintained in optimal joint alignment during the application of a cast including:
    a base;
    a cylindrical upright supported by the base; and
    a limb-support assembly adjustably mounted on the upright, said assembly including a tubular member slidable up, down and around the upright, and an elongated limb-rest pivotally mounted on the tubular member, said limb-rest being pivotable about its own long axis, said tubular member having a clamping arrangement at one end for clamping the tubular member in the desired position on the upright, said tubular member further having a ball-like support with a projecting dowel at the other end for pivotally supporting the limb-rest, said limb-rest having a limb-supporting tongue engaged to an opposed clamping member on opposite sides of the ball-like support and on opposite sides of the dowel, said limb-rest further having clamping means for clamping the limb-supporting tongue and the opposed clamping member together to prevent rotation of the limb-rest about the ball-like support and the projecting dowel thereby positioning the limb-rest at a desired angle relative to its long axis, and said limb-rest further having means to releasably engage one of a plurality of different limb-positioning attachment.

15. The orthopedic casting apparatus as claimed in claim 14 wherein one of the limb-support assembly and limb-positioning attachment is a sleeve that slides over the other.

16. The orthopedic casting apparatus as claimed in claim 14 or 15 wherein said opposed clamping member includes means for releaseably engaging one of a plurality of different limb-positioning attachment.

17. An orthopedic casting apparatus for use with a plurality of interchangeable limb-positioning attachments, whereby an extremity is maintained in optimal joint alignment during the application of a cast including:
    a base;
    a cylindrical upright supported by the base, said upright including two rods, one of which is capable of telescoping into the other and means to engage said rods at a desired length; and
    a limb-support assembly adjustably mounted on the upright, said assembly including a tubular member slidable up, down and around the upright, and an elongated limb-rest pivotally mounted on the tubular member, said limb-rest being pivotable about its own long axis, said tubular member having a clamping arrangement at on end for clamping the tubular member in the desired position on the upright, said tubular member further having a ball-like support with a projecting dowel at the other end for pivotally supporting the limb-rest, said limb-rest having a limb-supporting tongue engaged to an opposed clamping member on opposite sides of the ball-like support and on opposite sides of the dowel, said limb-rest futher having clamping means for clamping the limb-supporting tongue and the opposed clamping member together to prevent rotation of the limb-rest about the ball-like support and the projecting dowel therby positioning the limb-rest at a desired angle relative to its long axis, and said limb-rest further having means to releasably engage one of a plurality of different limb-positioning attachments.

18. The orthopedic casting apparatus as claimed in claim 17 wherein one of the limb-support assembly and limb-positioning attachment is a sleeve that slides over the other.

19. The orthopedic casting apparatus as claimed in claim 17 or 18 wherein said opposed clamping member includes means for releaseably engaging one of a plurality of different limb-positioning attachment.

* * * * *